United States Patent [19]

Croce et al.

[11] Patent Number: 5,674,682

[45] Date of Patent: Oct. 7, 1997

[54] NUCLEIC ACID PRIMERS FOR DETECTING MICROMETASTASIS OF PROSTATE CANCER

[75] Inventors: Carlo Croce, Philadelphia, Pa.; Leonard Gomella, Sewell, N.J.; S. Grant Mulholland, Gladwyne; Jose G. Moreno, Wayne, both of Pa.; Rainer Fischer, Aachen-Leniers, Germany

[73] Assignee: Thomas Jefferson University, Philadelphia, Pa.

[21] Appl. No.: 358,782

[22] Filed: Dec. 15, 1994

Related U.S. Application Data

[63] Continuation-in-part of Ser. No. 294,611, Aug. 23, 1994, Pat. No. 5,506,106, which is a continuation of Ser. No. 973,322, Oct. 29, 1992, abandoned.

[51] Int. Cl.$^6$ .......................... C07H 21/02; C07H 21/04; C12P 19/34; C12Q 1/68

[52] U.S. Cl. .......................... 435/6; 435/91.1; 435/91.2; 435/810; 536/23.1; 536/24.31; 536/24.33; 536/24.5

[58] Field of Search ........................ 435/6, 91.1, 91.2, 435/810; 536/23.1, 24.31, 24.33, 24.5

[56] References Cited

FOREIGN PATENT DOCUMENTS

WO 94/27152  11/1994  WIPO.

OTHER PUBLICATIONS

Lundwall, Bioch. Biophy. Res. Comm. 161(3): 1151–1159, 1989.
Schulz, Nuc. Acids Res. 16(13): 6226, 1988.
O'Garra, A. and Vieira, P., "Polymerase chain reaction for detection of cytokine gene expression", *Current Opinion in Immunology*, 1992, 4:211–215.

*Primary Examiner*—Stephanie W. Zitomer
*Assistant Examiner*—Paul B. Tran
*Attorney, Agent, or Firm*—Woodcock Washburn Kurtz Mackiewicz & Norris

[57] ABSTRACT

Oligonucleotides for and a method of diagnosing prostate micrometastasis are provided by the present invention whereby nucleic acids from a tissue sample from a patient are isolated, nucleic acids from the tissue sample specific for prostate cancer are amplified, or a signal generated by hybridization of a probe specific to a prostate cancer specific nucleic acid is amplified; and detection of amplified nucleic acids is indicative of micrometastasis of prostate cancer.

8 Claims, 5 Drawing Sheets

```
  1  AGCCCCAAGC TTACCACCTG CACCCGGAGA GCTGTGTCAC CATGTGGGTC   Exon 1
       ────PR5────►
 51  CCGGTTGTCT TCCTCACCCT GTCCGTGACG TGGATTGTGT GTGCAGCCCT
     ──────PR2──────►
101  CAGCCTTTCT CCGGATGTGG AGGCCAGGAC GTGCCAGGAC GATGCCCAAG   Exon 2
                 ────PR1────►        A(3)
151  CCTTCCAAGT GCTTCTGCCA TGTCTTGGGA GGGCATGTTG CGCCCATGCT
201  CTGTGCAGC CCCATGTGT GGTCAGAGCT GGGGACTGCA TCAAGAACAA
251  AAGCGTGATC TTGCTGGGTC GGCACAGCCT GTTTCATCCT GAAGACACAG
301  GCCAGGTATT TCAGGTCAGC CACAGCTTCC CACACCCGCT CTACGATATG
351  AGCCTCCTGA AGAATCGATT CCTCAGGCCA GGTGATGACT CCAGCCACGA   Exon 3
     ────PR3────►
401  CCTCATGCTG CTCCGCCTGT CAGAGCCTGC CGAGCTCACG GATGCTGTGA
                                                          A(3)
451  AGGTCATGGA CCTGCCCACC CAGGAGCCAG CACTGGGGAC CACCTGCTAC
501  GCCTCAGGCT GGGGCAGCAT TGAACCAGAG GAGTTCTTGA CCCCAAAGAA
551  ACTTCAGTGT GTGGACCTCC ATGTTATTTC CAATGACGTG TGTGCGCAAG   Exon 4
        ─PR1─►
601  TTCACCCTCA GAAGGTGACC AAGTTCATGC TGTGTGCTGG ACGCTGGACA
651  GGGGGCAAAA GCACCTGCTC GGGTGATTCT GGGGGCCCAC TTGTCTGTAA
                                                  ───PR7───►
701  TGGTGTGCTT CAAGGTATCA CGTCATGGGG CAGTGAACCA TGTGCCCTGC   Exon 5
     ─►                            ───PR8───►
751  CCGAAAGGCC TTCCCTGTAC ACCAAGGTGG TGCATTACCG GAAGTGGATC
                                              GT(4)       T(3)
801  AAGGACACCA TCGTGGCCAA CCCCCTGAGCA CCCCTATCAA CCCCCTATTG
                                                G(3)
851  TAGTAAACTT GGAACCTTGG AAATGACCAG GCCAAGACTC AAGCCTCCCC
901  AGTTCTACTG ACCTTTGTCC TTAGGTGTGA GGTCCAGGGT TGCTAGGAAA
951  AGAAATCAGC AGACACAGGT GTAGACCAGA GTGTTTCTTA
                                 ◄────PR4────
```

FIG. 2

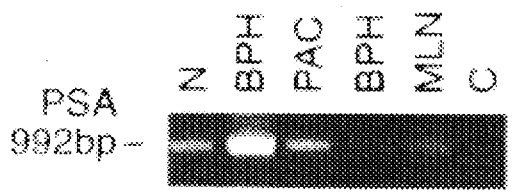

```
ATTCCGCCGG AGAGCTGTGT CACCATGTGG GTCCCGGTTG TCTTCCTCAC CCTGTCCGTG
                                                                60
ACGTGGATTG GTGCTGCACC CCTCATCCTG TCTCGGATTG TGGGAGGCTG GGAGTGCGAG
        80          90         100         110         120
AAGCATTCCC AACCCTGGCA GGTGCTTGTG GCCTCTCGTG GCAGGGCAGT CTGCGGGCGT
       140         150         160         170         180
GTTCTGGTGC ACCCCCAGTG GGTCCTCACA GCTGCCCACT GCATCAGGAA CAAAAGCGTG
       200         210         220         230         240
ATCTTGCTGG GTCGGCACAG CCTGTTTCAT CCTGAAGACA CAGGCCAGGT ATTTCAGGTC
       260         270         280         290         300
AGCCACAGCT TCCCACACCC GCTCTACGAT ATGAGCCTCC TGAAGAATCG ATTCCTCAGG
       320         330         340         350         360
CCAGGTGATG ACTCCAGCCA CGACCTCATG CTGCTCCGCC TGTCAGAGCC TGCCGAGCTC
       380         390         400         410         420
ACGGATGCTG TGAAGGTCAT GGACCTGCCC ACCCAGGAGC CAGCACTGGG GACCACCTGC
       440         450         460         470         480
TACGCCTCAG GCTGGGGCAG CATTGAACCA GAGGAGTTCT TGACCCCAAA GAAACTTCAG
       500         510         520         530         540
TGTGTGGACC TCCATGTTAT TTCCAATGAC GTGTGTGCGC AAGTTCACCC TCAGAAGGTG
       560         570         580         590         600
ACCAAGTTCA TGCTGTGTGC TGGACGCTGG ACAGGGGCA  AAAGCACCTG CTCGGGTGAT
       620         630         640         650         660
TCTGGGGGCC CACTTGTCTG TAATGGTGTG CTTCAAGGTA TCACGTCATG GGGCAGTGAA
       680         690         700         710         720
CCATGTGCCC TGCCCGAAAG GCCTTCCCTG TACACCAAGG TGGTGCATTA CCGGAAGTGG
       740         750         760         770         780
```

FIG.5B

```
         790        800        810        820        830        840
   ATCAAGGACA CCATCGTGGC CAACCCCTGA GCACCCCTAT CAACTCCCTA TTGTAGTAAA
         850        860        870        880        890        900
   CTTGGAACCT TGGAAATGAC CAGGCCAAGA CTCAAGCCTC CCCAGTTCTA CTGACCTTTG
         910        920        930        940        950        960
   TCCTTAGGTG TGAGGTCCAG GGTTGCTAGG AAAAGAAATC AGCAGACACA GGTGTAGACC
         970        980        990       1000       1010       1020
   AGAGTGTTTC TTAAAATGGTG TAATTTTGTC CTCTCTGTGT CCTGGGAAT ACTGGCCATG
        1030       1040       1050       1060       1070       1080
   CCTGGAGACA TATCACTCAA TTTCTCTGAG GACACAGATA GGATGGGGTG TCTGTGTTAT
        1090       1100       1110       1120       1130       1140
   TTGTGGGGTA CAGAGATGAA AGAGGGGTGG GTACCACACT GAGAGAGTGG AGAGTGACAT
        1150       1160       1170       1180       1190       1200
   GTGCTGGACA CTGTCCATGA AGCACTGAGC AGAAGCTGGA GGCACAACGC ACCAGACACT
        1210       1220       1230       1240       1250       1260
   CACAGCAAGG ATGGAGCTGA AAACATAACC CACTCTGTCC TGGAGGCACT GGGAAGCCTA
        1270       1280       1290       1300       1310       1320
   GAGAAGGCTG TGAGCCAAGG AGGGAGGGTC TTCCCTTTGGC ATGGGATGGG GATGAAGTAA
        1330       1340       1350       1360       1370       1380
   GGAGAGGGAC TGGACCCCCT GGAAGCTGAT TCACTATGGG GGGAGGTGTA TTGAAGTCCT
        1390       1400       1410       1420       1430       1440
   CCAGACAACC CTCAGATTTG ATGATTTCCT AGTAGAACTC ACAGAAATAA AGAGCTGTTA
        1450       1460
   TACGTGAAAA AAAACGGAAT CC
```

5,674,682

1

NUCLEIC ACID PRIMERS FOR DETECTING MICROMETASTASIS OF PROSTATE CANCER

REFERENCE TO RELATED APPLICATIONS

This application is a continuation in part of U.S. application Ser. No. 08/294,611, filed Aug. 23, 1994, now U.S. Pat. No. 5,506,106 which is a continuation of U.S. application Ser. No. 07/973,322, filed Oct. 29, 1992, now abandoned.

FIELD OF THE INVENTION

This invention is directed to methods of detecting prostate cancer micrometastasis.

BACKGROUND OF THE INVENTION

Prostate cancer metastasis will claim the lives of over 30,000 Americans this year. Boring et al., *Cancer Statistics* 1991, 19. The mode of dissemination however, remains very poorly understood. An almost dogmatic view of metastasis holds that prostate cancer cells first spread through the prostatic capsule then into the lymphatics, and eventually hematogenously travel to bone. Byar et al., *Cancer* 1972, 30, 5; Winter, C. C., *Surg. Gynecol. Obstet.* 1957, 105, 136; Hilaris et al., *Am. J. Roentgenol.* 1974, 121, 832; McLaughlin et al., *J. Urol.* 1976, 115, 89; Jacobs, S. C., *Urology* 1983, 21, 337; Batson, O. V., *Ann. Surg.* 1940, 112, 138; Saitoh et al., *Cancer* 1984, 54, 3078–3084; Whitmore, W. F., Jr., *Cancer* 1973, 32, 1104. However, this model has been based on histopathologic studies which have significant limitations, and in actuality the sequence of metastatic events remain unknown. Solid tumor animal experiments suggest that only 0.01% of circulating cancer cells eventually create a single metastatic deposit. Fidler et al., *Science* 1982, 217, 998–1001; Liotta et al., *Cancer Res.* 1974, 34, 997; Schirrmacher, B., *Adv. Cancer Res.* 1985, 43, 1–32. Ostensibly, a single bone metastasis from human prostatic adenocarcinoma (PAC) could be generated by 10,000 circulating cancer cells (2 cells/1 ml blood). In the past, detection of such a low concentration of cells has been difficult or impossible. Recently, however, Wu et al. used keratin-19 (K-19) mRNA PCR to detect breast cancer micrometastasis in patient lymph nodes and bone marrow. Wu et al., *Lab. Inv.* 1990, 62, 109A. Miyomura et al., also reported the detection of minimal residual acute lymphoblastic leukemia by PCR in patients harboring the Philadelphia chromosome. Miyomura et al., *Blood* 1992, 79, 1366–1370.

A method of detecting the micrometastasis of prostate cancer would be greatly desirable.

SUMMARY OF THE INVENTION

In accordance with the present invention, methods of detecting prostate cancer micrometastasis in a patient are provided comprising obtaining a sample comprising nucleic acids from a patient tissue sample; amplifying nucleic acids specific for prostate cancer or amplifying a signal generated by hybridization of a probe specific to a prostate cancer specific nucleic acid in said sample; and detecting the presence of amplified nucleic acids or amplified signal wherein the presence of amplified nucleic acids or amplified signal indicates micrometastasis of prostate cancer.

The scope of the present invention also includes a method of detecting cells which express prostate cancer specific sequences comprising obtaining a sample suspected of having prostate cancer specific sequences comprising nucleic acids; and detecting the presence of nucleic acids specific for prostate cancer or a signal specific for prostate cancer wherein the presence of nucleic acids or signal indicates prostate cancer.

Prostate cancer specific primer sequences such as and not limited to the sequences GAGGTCCACACACTGAAGTT (SEQ ID NO: 1) GCCTCCTGAAGAATCGATTCCT (SEQ ID NO: 2), GTTGTCTTCCTCACCCTGT (SEQ ID NO: 3); TAAGAAACACTCTGGTCT (SEQ ID NO: 4); AGC-CCCAAGCTTACCACCT (SEQ ID NO: 5); CACAATC-CGAGACAGGAT (SEQ ID NO: 6); GCCCACTTGTCTG-TAATG (SEQ ID NO: 7); CAGGGCACATGGTTCACT (SEQ ID NO: 8), TGGAGTCATCACCTGGCCTGAGGAA (SEQ ID NO: 9), and CCCAACCCTGGCAGGTGTTG-TAGC (SEQ ID NO: 10), may be used in the amplification procedure of the present invention. Isolated nucleic acid sequences of SEQ ID NOS: 1–10 are within the scope of the present invention.

BRIEF DESCRIPTION OF THE FIGURES

FIG. 2 displays the sequence of a 992 base pair prostate specific antigen (PSA) cDNA PCR fragment, SEQ ID NO: 13, obtained from prostate tissue. PSA exons are boxed. The shaded boxed sequence corresponds to the postulated binding site to macroglobulins. Oligonucleotide primer sequences are underlined. Variations observed in different PSA sequences in the EMBL data base are indicated in comparison with the sequence cDNA PCR fragment. Numbers in parenthesis in FIG. 2 refer to the sequences in the following references for the examined sequences: (1) Lundwall and Lilja, *FEBS Lett.*, 1987, 214, 317–322; (2) Digby, M. R., et al., *Nucleic Acids Res.*, 1989, 17, 2137; (3) Stucka, R. et al., *Nucleic Acids Res.*, 1988, 16, 6226; and (4) Klobeck, H. G., et al., *Nucleic Acids Res.*, 1989, 17, 3981, which were compared to the sequences of the present invention.

FIG. 3 is an ethidium bromide stained agarose gel of the PSA RT-PCR products from normal prostate tissue (lane 1), benign prostatic hypertrophy (BPH) (lanes 2 and 4), prostate adenocarcinoma (lane 3), and metastatic prostate cancer to a lymph node (lane 5). Lane 6 is a negative control. PCR was performed with PSA specific primers 4 (SEQ ID NO: 4) and 5 (SEQ ID NO: 5).

FIGS. 5A, and 5B are the sequence of PSA-20, the cDNA probe used in the detection of the amplified product in the methods of the present invention.

DETAILED DESCRIPTION OF THE INVENTION

Figures 1A, 1B, 1C:
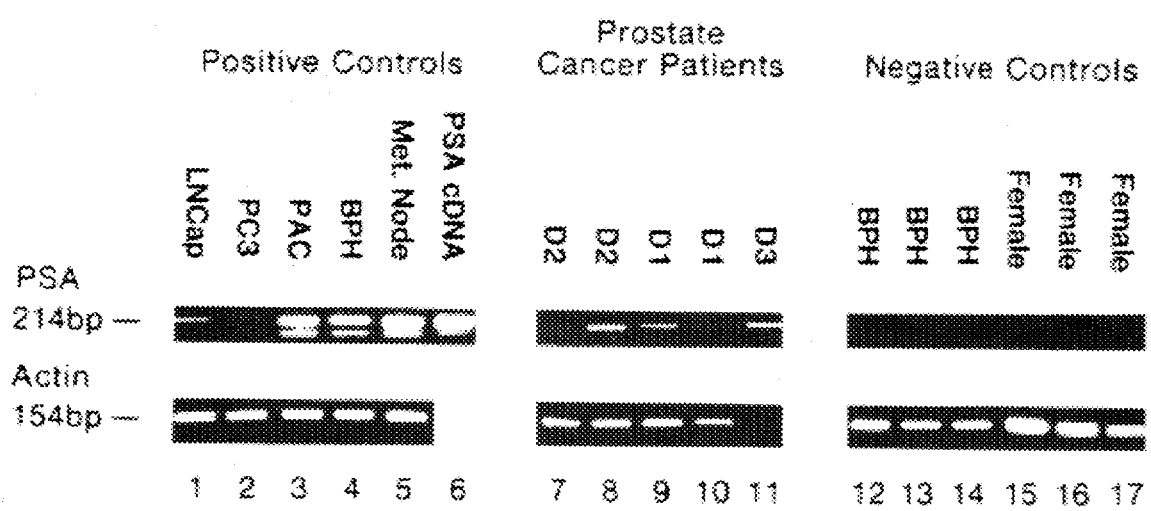
FIGS. 1A, 1B, and 1C show an agarose gel in which micrometastasis is indicated by the presence of a 214 base pair (bp) band.

In accordance with the present invention, methods of detecting prostate cancer micrometastasis in a patient are provided comprising obtaining a sample comprising nucleic acids from a patient tissue sample; amplifying nucleic acids specific for prostate cancer or amplifying a signal generated by hybridization of a probe specific to a prostate cancer specific nucleic acid in said sample; and detecting the presence or absence of amplified nucleic acids or amplified signal wherein the presence of amplified nucleic acids or amplified signal indicates micrometastasis of prostate cancer.

The scope of the present invention also includes a method of detecting cells which express prostate cancer specific sequences comprising obtaining a sample suspected of having prostate cancer specific sequences comprising nucleic acids; and detecting the presence of nucleic acids specific for prostate cancer or a signal specific for prostate cancer wherein the presence of nucleic acids or signal indicates prostate cancer.

The method of detecting cells which express prostate cancer specific sequences comprises amplifying nucleic acids specific for prostate cancer or amplifying a signal generated by hybridization of a probe specific to a prostate cancer specific nucleic acid in said sample; and detecting the presence of the amplified nucleic acids or the amplified signal wherein the presence of amplified nucleic acids or amplified signal indicates micrometastasis of prostate cancer.

A patient suspected of prostate cancer micrometastasis includes a patient diagnosed with prostate cancer who may or may not have experienced symptoms associated with metastasis and who has not been able to be diagnosed by other available methods, such as bone scan and imaging studies, as having micrometastatic or metastatic prostate cancer. In accordance with methods of the present invention, methods of detecting micrometastasis of prostate cancer in a patient are provided comprising obtaining a patient tissue sample for testing. The tissue sample may be solid or liquid, a body fluid sample such as and not limited to saliva, sputum, mucus, bone marrow, serum, blood, urine, lymph, tears, semen, or feces from a patient suspected of having prostate cancer. In addition, a tissue sample such as a malignant or benign tumor, prostate tumor for example, or a may be provided for the detection of prostate cancer micrometastasis in accordance with the present invention.

Nucleic acids, such as DNA (including cDNA) and RNA (including mRNA), are obtained from the patient sample. Preferably RNA is obtained from a blood sample, such as and not limited to a peripheral venous blood sample. A whole blood gradient may be performed to isolate nucleated cells and total RNA is extracted such as by the RNazole B method (Tel-Test Inc., Friendswood, Tex.) or by modification of any method known in the art such as described in Sambrook et al., *Molecular Cloning: A Laboratory Manual* (Cold Spring Harbor Laboratory, Cold Spring Harbor, N.Y., 1989), incorporated herein by reference in its entirety.

Nucleic acid extraction is followed by amplification of the same by any technique known in the art. The amplification step includes the use of at least one primer sequence which is complementary to a portion of a prostate cancer specific sequence. Prostate cancer specific sequences are defined for purposes of the present invention to include (and are not limited to) prostate specific antigen (PSA), prostate specific membrane antigen (PSM), prostatic acid phosphotase (PAP), and keratin-19 sequences.

Sequences useful in the amplification methods include and are not limited to GAGGTCCACACACTGAAGTT (SEQ ID NO: 1) and GCCTCCTGAAGAATCGATTCCT (SEQ ID NO: 2), GTTGTCTTCCTCACCCTGT (SEQ ID NO: 3); TAAGAAACACTCTGGTCT (SEQ ID NO: 4); AGCCCCAAGCTTACCACCT (SEQ ID NO: 5); CACAATCCGAGACAGGAT (SEQ ID NO: 6); GCCCACTTGTCTGTAATG (SEQ ID NO: 7); CAGGGCACATGGTTCACT (SEQ ID NO: 8), TGGAGTCATCACCTGGCCTGAGGAA (SEQ ID NO: 9), and CCCAACCCTGGCAGGTGTTGTAGC (SEQ ID NO: 10). A Gene Bank version-70. (Mountain View, Calif.) search confirmed the specificity of these primers to PSA and not to the human glandular kallikrein (HMGK) gene which has high homology to the PSA gene. Henttu et al, *Biochem. Biophys. Res. Comm.* 1989, 160, 903–910, incorporated herein by reference in its entirety. PSA2 (SEQ ID NO: 1) and PSA3 (SEQ ID NO: 2) bind sequences that span intron III of the PSA gene such that PCR amplification yields a 360 bp DNA and a 214 bp RNA product, thereby eliminating the possibility of false positives from DNA contamination. Oligonucleotide primers may be prepared by any method known in the art such as by standard phosphoramidite chemistry. (See Sambrook et al., supra).

Amplification may use oligonucleotides which are complementary to prostate specific antigen gene which do not hybridize to human glandular kallikrein gene. Where a template dependent process of amplification uses a pair of primers, one primer of the pair may comprise oligonucleotides which are complementary to nucleic acid sequences which encode prostate cancer specific proteins. The one primer of the pair may be selected from the group consisting of SEQ ID NOS: 1, 2, 3, 4, 5, 6, 7, 8, 9, and 10.

Alternatively, each of the two oligonucleotides in the primer pair may be specific to a nucleic acid sequence which encodes a prostate cancer specific protein. The primers may be designed to be complementary to separate regions of the prostate specific antigen (PSA) gene, for example. Henttu et al., *Biochem. Biophys. Res. Comm.* 1989, 160, 903–910, incorporated herein by reference in its entirety. By separate regions is meant that a first primer is complementary to a 3' region of the PSA gene and a second primer is complementary to a 5' region of the PSA gene. Preferably, the primers are complementary to distinct, separate regions and are not complementary to each other. The primers of SEQ ID NOS: 1–10 are merely exemplary of the primers which may be useful in the present invention.

When an amplification method includes the use of two primers, such as the polymerase chain reaction, the first primer may be selected from the group consisting of SEQUENCE ID NOS: 2, 3, 5, 7, and 10, and the second, primer may be selected from the group consisting of SEQUENCE ID NOS: 1, 4, 6, 8, and 9. Any primer pairs which transcribe nucleic acids toward each other and which are specific for prostate cancer may be used in accordance with the methods of the present invention.

Total extraction of RNA is preferably carried out. As used herein, the term "amplification" refers to template-dependent processes and vector-mediated propagation which result in an increase in the concentration of a specific nucleic acid molecule relative to its initial concentration, or in an increase in the concentration of a detectable signal. As used herein, the term template-dependent process is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, J. D. et al., In: Molecular Biology of the Gene, 4th Ed., W. A. Benjamin, Inc., Menlo Park, Calif. (1987) incorporated herein by reference in its entirety). Typically, vector mediated methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., Molecular Cloning (A Laboratory Manual), Cold Spring Harbor Laboratory, 1982, each incorporated herein by reference in its entirety.

A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159, and in Innis et al., *PCR Protocols*, Academic Press, Inc., San Diego Calif., 1990, each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of mRNA amplified. Polymerase chain reaction methodologies are well known in the art.

Another method for amplification is the ligase chain reaction (referred to as LCR), disclosed in EPA No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Application No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]triphosphates in one strand of a restriction site (Walker, G. T., et al., *Proc. Natl. Acad. Sci. (U.S.A.)* 1992, 89:392–396, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Prostate specific sequences can also be detected using a cyclic probe reaction (CPR). In CPR, a probe having a 3' and 5' sequences of non-prostate specific DNA and middle sequence of prostate specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a prostate cancer specific expressed nucleic acid.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS) (Kwoh D., et al., *Proc. Natl. Acad. Sci. (U.S.A.)* 1989, 86:1173, Gingeras T. R., et al., PCT Application WO 88/10315, incorporated herein by reference in their entirety), including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has prostate specific sequences. Following polymerization, DNA/RNA hybrids are digested with RNase H while double stranded DNA molecules are heat denatured again. In either case the single stranded DNA is made fully double stranded by addition of second prostate specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate prostate cancer specific sequences.

Davey, C., et al., European Patent Application Publication No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT Application WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., In: *PCR Protocols: A Guide to Methods and Applications* 1990, Academic Press, New York) and "one-sided PCR" (Ohara, O., et al., *Proc. Natl. Acad. Sci. (U.S.A.)* 1989, 86:5673–5677), all references herein incorporated by reference in their entirety.

Methods based on ligation of two (or more) oligonucleotides in the presence of nucleic acid having the sequence of the resulting "di-oligonucleotide", thereby amplifying the di-oligonucleotide (Wu, D. Y. et al., *Genomics* 1989, 4:560, incorporated herein by reference in its entirety), may also be used in the amplification step of the present invention.

Following amplification, the presence or absence of the amplification product may be detected. The amplified product may be sequenced by any method known in the art, including and not limited to the Maxam and Gilbert method, see Sambrook, supra. The sequenced amplified product is then compared to a sequence known to be in a prostate cancer specific sequence. Alternatively, the nucleic acids may be fragmented into varying sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labelled probe is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 200 nucleotides in length, and more preferably about 1462 nucleotides in length. The probe may have the sequence set forth in FIGS. 5A, and 5B (SEQ ID NO: 13), or a sequence similar to that set forth in FIGS. 5A, and 5B, for example. Mismatches which permit substantial similarity to SEQ ID NO: 13, such as and not limited to sequences with similar hydrophobicity and hydrophilicity, will be known to those of skill in the art once armed with the present disclosure. Various labels for visualization or detection are known to those of skill in the art, such as and not limited to fluorescent staining, ethidium bromide staining for example, avidin/biotin, radioactive labeling such as $^{32}P$ labeling, and the like. Preferably, the product, such as the PCR product, may be run on an agarose gel and visualized using a stain such as ethidium bromide. See Sambrook et al., supra. The matrix may then be analyzed by autoradiography to locate particular fragments which hybridize to the probe.

A diagnostic kit for detecting micrometastasis of prostate cancer comprising in one or more containers at least one primer which is complementary to a prostate cancer specific sequence and a means for visualizing amplified DNA is also within the scope of the present invention. Alternatively, the kit may comprise two primers. In either case, the primers may be selected from the group consisting of SEQ ID NOS: 1–10, for example. The diagnostic kit may comprise a pair of primers wherein one primer within said pair is complementary to a region of the prostate specific antigen gene, wherein one of said pair of primers is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, a probe specific to the amplified product, and a means for visualizing amplified DNA, and optionally including one or more size markers, and positive and negative controls. The diagnostic kit of the present invention may comprise one or more of a fluorescent dye such as ethidium bromide stain, rip, and biotin, as a means for visualizing or detecting amplified DNA. Optionally the kit may include one or more size markers, positive and negative controls, and/or a probe specific to the amplified product.

The present invention is also directed to isolated nucleic acid sequences including and are not limited to the nucleic acid sequences GAGGTCCACACACTGAAGTT (SEQ ID NO: 1) GCCTCCTGAAGAATCGATTCCT (SEQ ID NO: 2), GTTGTCTTCCTCACCCTGT (SEQ ID NO: 3); TAAGAAACACTCTGGTCT (SEQ ID NO: 4); AGCCCAAGCTTACCACCT (SEQ ID NO: 5); CACAATCCGAGACAGGAT (SEQ ID NO: 6); GCCCACTTGTCTGTAATG (SEQ ID NO: 7); CAGGGCACATGGTTCACT (SEQ ID NO: 8), TGGAGTCATCACCTGGCCTGAGGAA (SEQ ID NO: 9), and CCCAACCCTGGCAGGTGTTGTAGC (SEQ ID NO: 10). Contemplated by this definition are oligonucleotides of about 10 to about 20 codons within the coding sequence for prostate specific antigen gene. In addition, mismatches within the sequences identified above, which achieve the methods of the invention, such that the mismatched sequences are substantially similar to and thus hybridizable with the sequences identified above as SEQ ID NOS: 1–10, are also considered within the scope of the disclosure. Mismatches which permit substantial similarity to any one of SEQ ID NOS: 1–10, such as and not limited to sequences with similar hydrophobicity and hydrophilicity, will be known to those of skill in the art once armed with the present disclosure. The oligonucleotides may also be unmodified or modified.

The following examples are illustrative but are not meant to be limiting of the invention.

EXAMPLES

Example 1

Patient Specimens

Selection of cases was based on the following criteria. Prostate cancer patients were chosen for analysis if they had: (1) clinically and/or surgically staged D0–D2 disease (D0= elevated tumor markers with no demonstrable metastasis, D1=pelvic lymph node involvement, D2=disseminated disease usually to bone) without having received prior hormonal therapy and who had an elevated serum PSA, or (2) stage D3 disease (D2 disease that is refractory to hormonal therapy) with an elevated PSA. Negative control patients consisted of female volunteers, and patients with benign prostatic hypertrophy (BPH) proven by biopsy or men who were on a BPH study protocol. Patients who had surgical manipulation of the prostate during the previous year were excluded from the study. Positive controls included a lymph node from a patient with known metastatic PAC tissue from pathologically proven BPH and cDNA PSA plasmid. Henttu et al, *Biochem. Biophys. Res. Comm.* 1989, 160, 903–910. The protocol was approved by the Internal Review Board of Thomas Jefferson University Hospital and written consent was obtained. LNCAP and PC3 human cell lines were obtained from The American Type Culture Collection, (Rockville, Md.).

Example 2

Blood Preparation for RNA Extraction

Approximately six ml of venous blood were obtained with a standard venipuncture technique using heparinized tubes. Whole blood was mixed with an equal volume of phosphate buffered saline (PBS) which was then layered over eight ml of FICOLL(™) (Pharmacia Uppsala, Sweden) in a 15 ml polystyrene tube. The gradient was centrifuged at 200 g for 30 minutes at 5° C. The lymphocyte and granulocyte layer (approximately 5 ml) was carefully aspirated and re-diluted up to 50 ml with PBS in a 50 ml tube which was then centrifuged at 1800 g for 20 minutes a 5° C. Supernatant was discarded, and the pellet containing nucleated cells was used for RNA extraction using the RNazole B method, as described by the company (Tel-Test Inc., Friendswood, Tex.).

Example 3

Oligonucleotide primers and probes

PSA2 (5-GAGGTCCACACACTGAAGTT, SEQ ID NO: 1) and PSA3 (5-CCTCCTGAAGAATCGATTCCT, SEQ ID NO: 2) oligonucleotide primers were custom designed with high specificity to the PSA gene; a Gene Bank version-70 (Mountain View, Calif.) search confirmed the specificity of these primers to PSA and not to the human glandular kallikrein (HMGK) gene which has 75–85% homology to the PSA gene. Henttu et al, *Biochem. Biophys. Res. Comm.* 1989, 160, 903–910. The primers were synthesized and gel purified by the City of Hope DNA Synthesis Laboratory (Duarte, Calif.). PSA2 (SEQ ID NO: 1) and PSA3 (SEQ ID NO: 2) bind sequences that span intron III such that PCR amplification yielded a 360 bp DNA and a 214 bp RNA product. Previously published actin PCR primer sequences were used to rule out degraded RNA, and amplification with actin oligonucleotide primers A1 TCATCACCATTG-GCAATGAG (SEQ ID NO: 11) and A2 CACTGTGTTG-GCGTACAGGT (SEQ ID NO: 12) yielded a 154 bp RNA and a 250 bp DNA product. Ben-Ezra et al., *J. Histochem Cytochem.* 1991, 39, 351–354, incorporated herein by reference in its entirety.

Example 4

Reverse Transcriptase Reaction and Polymerase Chain Reaction

The reverse transcriptase reaction and PCR amplification were performed sequentially without interruption in a Perkin Elmer 9600 PCR machine (Emeryville, Calif.). 400 ng of total RNA in 20 µl DEPC (Diethyl-pyrocarbonate)-treated water were placed in a 65° C. water bath for five minutes then quickly chilled on ice immediately prior to the addition of PCR reagents. The 50 µl total PCR volume consisted of 2.5 units Taq polymerase (Perkin Elmer, Emeryville, Calif.), 2 units AMV reverse transcriptase (Boehringer Mannheim, Indianapolis, Ind.), 200 µM each of dCTP, dATP, dGTP, and dTTP (Perkin Elmer, Emeryville, Calif.), 18 pM each primer, 10 mM Tris-HCL, 50 mM KCl, and 2 mM $MgCl_2$ (Perkin Elmer, Emeryville, Calif.). PCR conditions were as follows: cycle 1 was performed at 42° C. for 15 minutes, then 97° C. for 15 seconds (one cycle); cycle 2 was performed at 95° C. for one minute, then 60° C. for one minute and 72° C. for 30 seconds (15 cycles); cycle 3 was performed at 95° C. for one minute, then 60° C. for one minute, and 72 degrees for one minute (10 cycles); cycle 4 was performed at 95° C. for one minute, then 60° C. for one minute and 72° C. for two minutes (8 cycles); cycle 5 was 72° C. for 15 minutes (one cycle); and the final cycle was held at 4° C. until the sample was taken out of the machine. The 50 µl PCR products were concentrated down to 10 µl with vacuum centrifugation and the entire sample was then run on a thin three percent Tris-borate-EDTA (TBE) agarose gel containing ethidium bromide. All specimens were analyzed at least twice to confirm a positive or negative outcome.

The potential risk of false positives from cross contamination was avoided by performing RT PCR in a single tube without interruption and using filtered pipet tips. Sensitivity was enhanced by using high amounts of Taq polymerase, progressively increasing extension times, and analyzing the entire 50 µl PCR product on thin ethidium bromide agarose gels. These measures ensured a high fidelity assay while maintaining technical simplicity.

Prostate human tissue specimens, tissue culture cell lines and a PSA cDNA plasmid, cloned and described by Henttu and Vihko; Henttu et al., *Biochem. Biophys. Res. Comm.* 1989, 160, 903–910, were used as positive controls, and they demonstrated the 214 bp bands as shown in FIG. 1, top panel. A pelvic lymph node with metastatic prostatic adenocarcinoma (PAC), a primary prostate cancer, and a BPH specimen all produced strong PSA PCR signals. The LNCAP and PC-3 human prostate cell lines produced weaker signals.

Example 5

Sequencing

Specificity of the primers to the PSA gene was confirmed with DNA sequence analysis of the amplified 214 bp fragment (FIG. 1 bottom panel) which in this segment had very little homology to the human glandular kallikrein, HMGK, gene.

The 214 bp product was purified with a Qiagen PCR Product Purification kit (Qiagen, Chatsworth, Calif.) as described by the manufacturer. One microgram of the PCR product underwent a PCR sequencing reaction by using the Taq DyeDeoxy Terminator Cycle sequencing kit in a Perkin-Elmer 9600 PCR Machine, as described by Applied Biosystems (Applied Biosystems, Foster, Calif.). The sequenced product was purified using centri-sep columns (Princeton Separations, Adelphia, N.J.) as described by the company. This product was then analyzed with an ABI Model 373A DNA sequencing system (Applied Biosystems, Foster, Calif.) integrated with a Macintosh IIci computer.

Example 6

Detection of Circulating Hematogenous Micrometastasis

Twelve prostate cancer patients and 17 control patients underwent RT PCR analysis on PSA and actin RNA extracted from blood, as described in Examples 1 through 4. The results are reported in Table 1. All cases demonstrated satisfactory RNA quality by actin PCR (FIG. 1, bottom row).

Of the 12 human prostatic adenocarcinoma (PAC) patients with metastatic disease, four cases (33%) had positive PSA signals indicating the presence of prostatic epithelial cells in the peripheral venous blood. These four cases consisted of two stage D1 patients, one stage D2 patient, and one stage D3 patient (N=1) (FIG. 1, top row). The 17 negative controls, which consisted of eight volunteer women and nine men with BPH, all had undetectable PSA mRNA by RT PCR. These data indicate that RT PCR of the PSA RNA gene can be used to specifically detect circulating hematogenous micrometastasis in patients with stage D1–D3 pathology. These findings are in agreement with studies by Hamby et al. who detected circulating PSA positive cells in patients with metastatic prostate cancer by flow cytology and immunohistology. Hamby et al., *Br. J. Urol.* 1992, 69, 392–396, incorporated herein by reference in its entirety.

Micrometastasis was not detected in eight of twelve prostate cancer patients consisting of two stage D3 patients, two stage D1 patients, and four stage D0 patients. Results indicate that the prostate cancer cells may be more concentrated in the "buffy coat" of the FICOLL(™) gradient. The PSA signal was stronger in the RNA extracted from cells obtained only from the "buffy coat" (FIG. 1, lane 8) compared to those isolated from the entire FICOLL(™) layer (FIG. 1, lane 7) in the same prostate cancer patient. These findings are in agreement with those of Harry et al. who found that prostatic epithelial cells migrate into the "buffy coat" Harry et al., *J. Surg. Res.* 1979, 26, 411–416, incorporated herein by reference in its entirety. In order to enhance the detection of micrometastasis, analysis may thus focus on these buffy coat cells.

TABLE 1

HEMATOGENOUS MICROMETASTASIS SUMMARY

| | Prostate Cancer Patients | | | Control Patients | |
|---|---|---|---|---|---|
| Stage | No. of Patients | Positive PSA/PCR | Source | No. of Patients | Positive PSA/PCR |
| D0 | 4 | 0 | Females BPH | 8 | 0 |
| D1 | 4 | 2 | | 9 | 0 |
| D2 | 1 | 1 | | | |
| D3 | 3 | 1 | | | |
| Total | 12 | 4 (33%) | | 17 | 0 |

Figure 4:
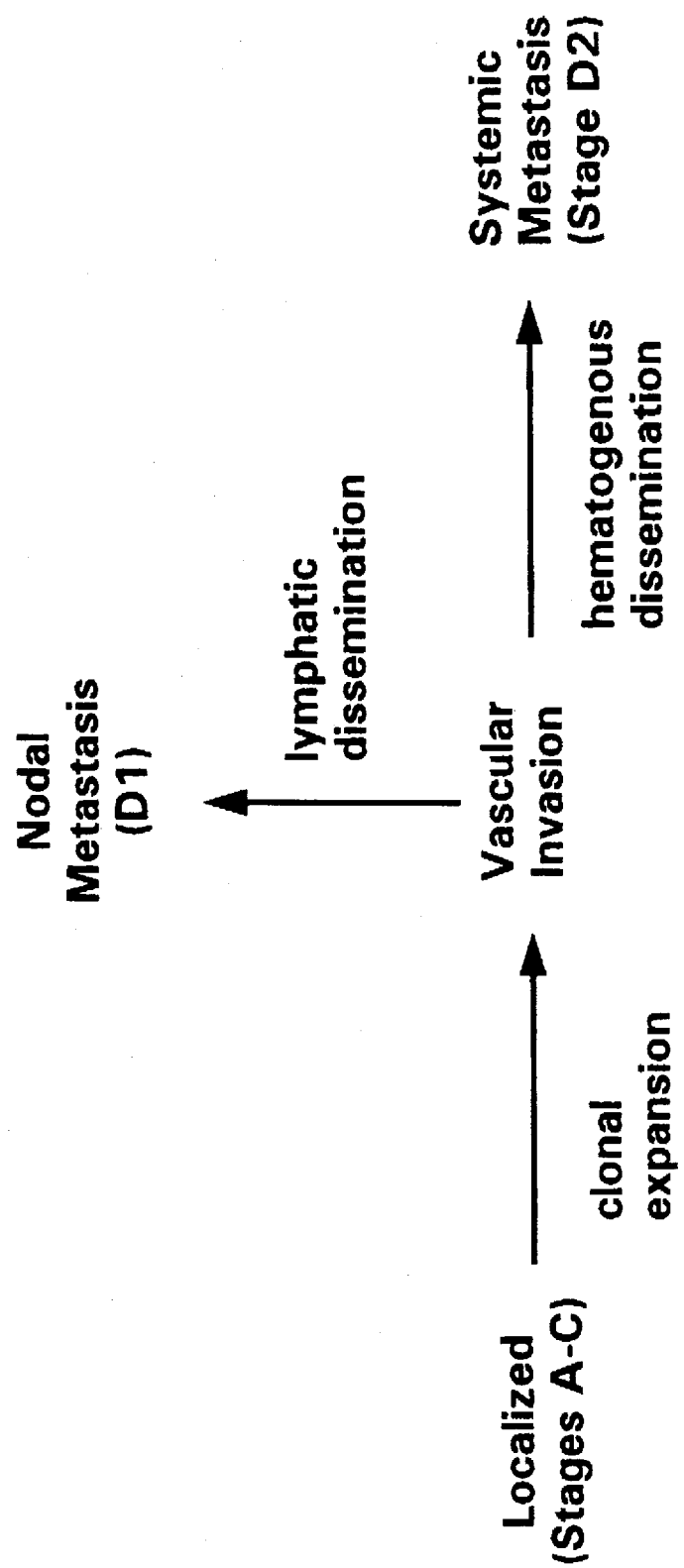
FIG. 4 displays a possible pattern of prostate cancer metastasis.

These data support animal experimental work suggesting that only the fittest tumor cells survive the metastatic cascade. A large number of circulating cancer cells (greater than 10,000 cells in a 70 kg human) may be required in order for a small percentage (less than 0.01%) of cells to survive and create a metastatic deposit. The finding of cancer cells in the peripheral venous blood suggests that these cells circulate through all organ capillary beds while forming metastatic colonies almost exclusively in bone. These data lend credence to the theory that the distribution of prostate cancer metastasis is determined by organ tropism, and not strictly anatomic factors such as Batson's vertebral venous plexus. Organ tropism may be determined by (a) preferential growth of cells in certain organs, (b) preferential adherence of cells to certain endothelial structures, and (c) chemotaxis. Finally, the discovery of prostate cancer cells in circulation of patients with D1 pathology calls into question the hypothesis that blood metastasis is a terminal event in the natural history of prostate cancer metastasis. To the contrary, these data point to the possibility that prostate cancer cells may spread to the neurovascular structures and then into the blood circulation, and lymphatic spread may be an associated event that is not an essential step for dissemination, FIG. 4.

Example 7

Patient Specimens

Analysis was performed on five prostate specimens from three patients. Histologically confirmed normal, benign prostatic hypertrophy (BPH), and adenocarcinoma tissue samples were obtained all within the same gland from a single patient undergoing radical prostatectomy for localized prostate cancer. The BPH tissue was also procured after transurethral prostatectomy in a second patient with a serum PSA of 4 ng/ml. A metastatic prostate cancer specimen was obtained from a grossly diseased iliac node taken during a laparoscopic pelvic lymph node dissection in a third patient with stage D1 disease and a serum PSA of 27 ng/ml. immediately after removal, tissues were stored at −70° C. prior to RNA extraction.

RNA Extraction

Total RNA extraction was performed using the RNazol B method as described by the manufacturer (Tel-Test, Inc., Friendswood, Tex.). Tissue samples were lysed in 3 ml RNAzol B and a homogenizer was applied to facilitate lysis when necessary. After addition of 0.3 ml of chloroform, the samples were vortexed and centrifuged at 12,000 g for 15 minutes at 4° C. The upper phase, containing total cellular RNA, was carefully removed and precipitated for 15 minutes with one volume of isopropyl alcohol. The pellet was rinsed twice with cold 75% ethanol, dried briefly in a speedvac apparatus and dissolved in 50–200 μl of water.

cDNA Synthesis

Total RNA (2 mg) was used for the synthesis of the first strand of complementary DNA (cDNA) using the SuperScript II reverse transcriptase (GIBCO-BRL). Total RNA from all specimens was isolated and reverse transcribed to cDNA using a primer having the sequence of SEQ ID NO: 4, specific for the PSA 3' untranslated region (nucleotides 992–972). Briefly, RNA and 20 pM of PSA primer 4 (SEQ ID NO: 4) were first denatured for 5 minutes at 70° C., chilled on ice for one minute and then incubated for one hour at 42° C. in 20 ml of a reaction mixture containing 1× first strand buffer, 250 mM/L dTNPs, 10 mM DTT and 200 U of SuperScript II reverse trancriptase.

Oligonucleotide Primers

Oligonucleotide sequences, GAGGTCCACACACT-GAAGTT (SEQ ID NO: 1) GCCTCCTGAAGAATCGAT-TCCT (SEQ ID NO: 2), GTTGTCTTCCTCACCCTGT (SEQ ID NO: 3); TAAGAAACACTCTGGTCT (SEQ ID NO: 4); AGCCCCAAGCTTACCACCT (SEQ ID NO: 5); CACAATCCGAGACAGGAT (SEQ ID NO: 6); GCCCACTTGTCTGTAATG (SEQ ID NO: 7); CAGGGCACATGGTTCACT (SEQ ID NO: 8), TGGAGT-CATCACCTGGCCTGAGGAA (SEQ ID NO: 9) and CCCAACCCTGGCAGGTGTTGTAGC (SEQ ID NO: 10); were chosen within PSA gene regions which maximize mismatches with other genes of the same family. SEQ ID NO: 2 has also been used with the first "G" deleted, such that the primer is also useful as a 21mer. The location of the primers is set forth in FIG. 2.

Polymerase Chain Reaction Procedure

One fifth of the cDNA preparation was amplified in 40 μl of PCR mix containing 1× PCR buffer (Boehringer Mannheim), 10 pM of each primer, 250 mM/L of dNTPs and 1.25 units of Taq DNA polymerase (Boehringer Mannheim). Each PCR cycle included denaturation at 94° C. for one minute (2 minutes for the first cycle), annealing at 56° C. for one minute and extension at 72° C. for two minutes (five minutes for the last extension). cDNA fragments were amplified using the same 3' primer of SEQ ID NO: 4 (PSA primer 4) with a primer specific for the first 20 nucleotides of the PSA cDNA SEQ ID NO: 5 (PSA primer 5). Thirty cycles were carried out using the PSA primers 5 and 4. PCR products were visualized in ethidium bromide stained 1.4% agarose gels and then purified using a gel extraction kit (Qiagen) following the manufacturer's instructions. The 992 bp PSA cDNA fragments, corresponding to the entire translated and part of the 3' untranslated region, were purified from preparative agarose gel electrophoresis and the DNA sequence was determined. This process was repeated with various combinations of primers set forth in FIG. 2, including primer combinations of SEQ ID NOS: 5 and 6, SEQ ID NOS: 1 and 6, SEQ ID NOS: 3 and 2, SEQ ID NOS: 7 and 8, SEQ ID NOS: 8 and 3, SEQ ID NOS: 8 and 1, SEQ ID NOS: 8 and 5, SEQ ID NOS: 4 and 7, SEQ ID NOS: 4 and 3, SEQ ID NOS: 4 and 1, and SEQ ID NOS: 4 and 5. Any of the primers with underlined arrows pointing toward each other (FIG. 2), which transcribe toward each other such that each strand is transcribed in the 3' direction, may be used together.

Sequencing

An automated 373A DNA sequencer (Applied Biosystems) and dye terminator kits from the same manufacturer were used for direct sequencing of the PSA cDNA fragments by the dideoxynucleotide chain termination method using fluorescent labels. The coding and non-coding strands of each fragment were sequenced with primers generating overlapping sequence data. The cDNA fragment was sequenced at least three times in both the 5' and 3' directions. Purity of cancer was ensured by analyzing a metastatic lymph node which would express PSA derived only from highly malignant prostatic cells.

Sequences were reassembled and analyzed using the SAP program. The normal, BPH, and prostate cancer cDNA sequence data of both strands were aligned and a computer analysis revealed 100% match with no evidence of mutation in prostate cancer as compared to normal tissue. Sequences were then compared to the published PSA cDNA sequences. The gene bank search demonstrated the following variations with the published PSA sequences: a dinucleotide (GT) deletion at position 38–39 when compared to Lundwall and Lilja's sequence (gene bank accession number x05332); a T to C at position 91 and an A to G at position 115 when compared to sequence number x13941, a G to A at position 169 and a G to A at position 843–844 after comparison with sequence number x14810. The perfect identity between our sequences obtained from 5 specimens in three different patients, suggests that the variations observed in the published sequences may be due to genetic polymorphisms or technical artifacts.

The complete coding sequence and part of the 3' untranslated PSA mRNA gene sequence isolated from BPH, normal, and malignant prostate tissue specimens were obtained and aligned. Computer analysis demonstrated an identical PSA cDNA match between the PSA expressed by BPH and normal tissue versus prostate cancer. The data indicates that a single genetic form of PSA is expressed in benign and malignant prostate tissue. It is possible that a mutated PSA gene might be specifically expressed in cells with bone invasive capabilities. Alternatively, the occurrence of altered PSA complexing and glycosylation in prostate cancer patients may be a result of post-translational events.

Various modifications of the invention in addition to those shown and described herein will be apparent to those skilled in the art from the foregoing description. Such modifications are also intended to fall within the scope of the appended claims.

What is claimed is:

1. An oligonucleotide consisting of a nucleic acid sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

2. An oligonucleotide consisting of a nucleic acid sequence selected from the group consisting of SEQ ID NO: 1 and SEQ ID NO: 2.

3. An oligonucleotide consisting of the nucleic acid sequence set forth in SEQ ID NO: 9.

4. An oligonucleotide consisting of the nucleic acid sequence set forth in SEQ ID NO: 10.

5. A diagnostic kit comprising in one or more containers, a pair of primers, wherein one of the primers within said pair is capable of hybridizing to a region of the prostate specific antigen gene but does not hybridize to human glandular kallikrein gene, and a means for visualizing amplified DNA.

6. The diagnostic kit of claim 5 wherein said means for visualizing amplified DNA is selected from the group consisting of ethidium bromide stain, $^{32}$P, and biotin.

7. A diagnostic kit for detecting prostate cancer comprising in one or more containers, a pair of primers, wherein one of the primers within said pair is capable of hybridizing to a region of the prostate specific antigen gene but does not hybridize to human glandular kallikrein gene, wherein said primer is selected from the group consisting of SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10, and a means for visualizing amplified DNA.

8. The diagnostic kit of claim 7 wherein said means for visualizing amplified DNA is selected from the group consisting of ethidium bromide stain, $^{32}$P, and biotin.

* * * * *

UNITED STATES PATENT AND TRADEMARK OFFICE
CERTIFICATE OF CORRECTION

PATENT NO. : 5,674,682

DATED : October 7, 1997

INVENTOR(S) : Croce et al.

Page 1 of 5

It is certified that error appears in the above-indentified patent and that said Letters Patent is hereby corrected as shown below:

On the cover page, Item [56]:
U.S. PATENT DOCUMENTS, please insert the following: --

| | | | |
|---|---|---|---|
| 4,446,122 | 5/1984 | Chu et al. | 424/1.1 |
| 4,803,169 | 2/1989 | Linsley et al. | 435/7 |
| 5,153,118 | 10/1992 | Wright, Jr. et al. | 435/7.23 |
| 5,085,983 | 2/1992 | Scanlon | 438/6 -- |

On the cover page, Item [56]:
FOREIGN PATENT DOCUMENTS, please insert the following: --

| | | |
|---|---|---|
| WO 90/02203 | 3/1990 | PCT |
| 0 520 794 A1 | 6/1992 | European Pat. Off. |
| 93 09966.1 | 5/1993 | PCT |
| 9314623.1 | 7/1993 | PCT -- |

On the cover page, second column under References Cited, OTHER PUBLICATIONS, please insert the following: --

Deguchi et al. Detection of Micrometastatic Prostate Cancer Cells in Lymph Nodes by Reverse Transcriptase-Polymerase Chain Reaction *Cancer Res* 1993 53:5350-5354

Hardingham et al. Immunobead-PCR: A Technique for the Detection of Circulating Tumor Cells Using Immunomagnetic Beads and the Polymerase Chain Reaction *Cancer Res* 1993 53:3455-3458

Israeli et al. Expression of the Prostate-specific Membrane Antigen *Cancer Res* 1994 54:1807-1811

Israeli et al. Molecular Cloning of a Complementary DNA Encoding a Prostate-specific Membrane Antigen *Cancer Res.* 1993 53:227-230

UNITED STATES PATENT AND TRADEMARK OFFICE
CERTIFICATE OF CORRECTION

PATENT NO. : 5,674,682
DATED : October 7, 1997
INVENTOR(S) : Croce et al.

It is certified that error appears in the above-identified patent and that said Letters Patent is hereby corrected as shown below:

Katz et al. Molecular Staging of Prostate Cancer with the Use of An Enhanced Reverse Transcriptase-PCT Assay *Urology* 1994 43:765-774

Mattano et al. Sensitive Detection of Rare Circulating Neuroblastoma Cells by the Reverse Transcriptase-Polymerase Chain Reaction *Cancer Res* 1992 52:4701-4705

Naito et al. Detection of Tyrosine Hydroxylase mRNA and Minimal Neuroblastoma Cells by the Reverse Transcription-Polymerase Chain Reaction *Euro J. Cancer* 1991 27:765-770

Schoenfeld et al. Detection of Breast Cancer Micrometastases in Axillary Lymph NOdes by Using Polymerase Chain Reaction *Cancer Res* 1994 54:2986-2990

Sharief et al. Human Prostatic Acid Phosphatase: cDNA Cloning, Gene Mapping and Protein Sequence Homology with Lysosomal Acid Phophatase *Biochem Biophys Res Commun* 1989 160:79-86

Smith et al. Detection of melanoma cells in peripheral blood by means of reverse transcriptase and polymerase chain reaction *The Lancet* 1991 338:1227-1229

Yokota et al. Use of Polymerase Chain Reactions to Monitor Minimal Residual Disease in Acute Lymphoblastic Leukemia Patients *Blood* 1991 77:331-339

Yu et al. Induction of prostate specific antigen production by steroids and tamoxifen in breast cancer cell lines *Breast Cancer Res and Treatment* 1994 32:291-300

Boring et al. Cancer Statistics, 1991 CA-A *Cancer Journal for Clinicians* 1991 41:19-36

Byar et al. Carcinoma of the prostate: Prognostic Evaluation of Certain Pathologic Features in 208 Radical Prostatectomies *Cancer* 1972 30:5-13

Winter C. The Problem of Rectal Involvement by Prostatic Cancer *Surg. Gynecol. Obstet* 1957 105:136-140

UNITED STATES PATENT AND TRADEMARK OFFICE
CERTIFICATE OF CORRECTION

PATENT NO. : 5,674,682

DATED : October 7, 1997

INVENTOR(S) : Croce et al.

Page 3 of 5

It is certified that error appears in the above-identified patent and that said Letters Patent is hereby corrected as shown below:

Hilaris et al. Radiation Therapy and Pelvic Node Dissection in the management of Cancer of the Prostate *Am. J. Roentgenol.* 1974 *121*:832-838

McLaughlin et al. Prostatic Carcinoma: Incidence and Location of Unsuspected Lymphatic Metastases *J. Urol.* 1976 *115*:89-94

Jacobs S. Spread of Prostatic Cancer to Bone *Urology* 1983 *21*:337-344

Batson O. The Function of the Vertebral Veins and Their Role in the Spread of Metastases *Ann. Surg.* 1940 *112*:138-149

Saitoh et al. Metastatic Patterns of Prostatic Cancer Correlation Between Sites and Number of Organs Involved *Cancer* 1984 *54*:3078-3084

Whitmore W. The Natural History of Prostatic Cancer *Cancer* 1973 *32*:1104-1112

Fidler et al. Biological Diversity in metastatic Neoplasms: Origins and Implications *Science* 1982 *217*:998-1001

Liotta et al. Quantitiative Relationships of Intravascular Tumor Cells, Tumor Vessels, and Pulmonary Metastases following Tumor Implantation *Cancer Res.* 1974 *34*:997-1004

Schirrmacher B. Cancer Metastasis: Experimental Approaches, theoretical Concepts, and Impacts for Treatment Strategies *Adv. Cancer Res.* 1985 *43*:1-73

Wu et al. Detection of Micrometastases in Breast Cancer by the Polymerase Chain Reaction: A Feasibility Study *Lab. Inv.* 1990 *62*:109A Miyamura et al. Detection of Philadelphia Chromosome-Positive Acute Lymphoblastic Leukemia by Polymerase Chain Reaction: Possible Eradication of Minimal Residual Disease by Marrow Transplantation *Blood* 1992 *79*:1366-1370

UNITED STATES PATENT AND TRADEMARK OFFICE
CERTIFICATE OF CORRECTION

PATENT NO. : 5,674,682

DATED : October 7, 1997

INVENTOR(S) : Croce et al.

It is certified that error appears in the above-identified patent and that said Letters Patent is hereby corrected as shown below:

Stamey et al. Prostate Specific Antigen in the Diagnosis and Treatment of Adenocarcinoma of the Prostate II. Radical Prostatectomy Treated Patients *J. Urol.* 1989 *141*:1076-1083

Ben-Ezra et al. Effect of Fixation on the Amplification of Nucleic Acids from paraffin-embedded Material by the Polymerase Chain Reaction *J. Histochem Cytochem.* 1991 *39*:351-354

Hamdy et al. Circulating Prostate Specific Antigen-positive Cells Correlate with metastatic Prostate Cancer *Br. J. Urol.* 1992 *69*:392-396

Harty et al. In Vitro Technique for Isolating Prostatic Cells from Blood *J. Surg. Res.* 1979 *26*:411-416

Henttu et al. cDNA Coding for the Entire Human Prostate Specific Antigen Shows High Homologies to the Human Tissue Kallikrein Genes *Biochem. Biophys. Res. Comm.* 1989 *160*:903-910

Watt et al. Human prostate-specific antigen: Structural and functional similarity with serine proteases *Proc. Natl. Acad. Sci USA* 1986 *83*:3166-3170

Lilja H. A Kalikrein-like Serine Protease in Prostatic Fluid Cleaves the Predominant Seminal Vesicle Protein *J. Clin. Invest.* 1985 *76*:1899-1903

Lundwall et al. Molecular cloning of human prostate specific antigen cDNA *FEBS letters* 1987 *214(2)*:317-322

Henttu et al. Expression Of The Gene Coding For Human Prostate-Specific Antigen and Related hGK-1 In Benign and malignant Tumors of The Human Prostate *Int. J. Cancer* 1990 *45*:654-660

Riegman et al. Molecular Cloning and Characterization of novel Prostate Antigen cDNA's *Biochem. Biophy. Res. Comm.* 1988 *155*:181-188

Christensson et al. Serum Prostate Specific Antigen Complexed to $\alpha$1-Antichymotrypsin as an Indicator of Prostate Cancer *J. Urology* 1993 *150*:100-105

UNITED STATES PATENT AND TRADEMARK OFFICE
CERTIFICATE OF CORRECTION

PATENT NO. : 5,674,682
DATED : October 7, 1997
INVENTOR(S) : Croce et al.

It is certified that error appears in the above-identified patent and that said Letters Patent is hereby corrected as shown below:

Barak et al. Binding of Serum Prostate Antigen to Concanavalin A in Patients with Cancer of Hyperplasia of the Prostate *Oncology* 1989 46:375-377

Moreno et al. Detection of Hematogenous Micrometastasis in Patients with Prostate Cancer *Cancer Res.* 1992 52:6110-6112 published October 27, 1992

Goblet et al. One-step amplification of transcripts in total RNA using the polymerase chain reaction *Nucleic Acids Res.* 1989 17:2144

Riegman et al. Characterization of the Prostate-Specific Antigen Gene: A Novel Human Kallikrein-Like Gene *Biochem. Biophys. Res. Comm.* 1989 159:95-102 van Krieken j. Prostate marker Immunoreactivity in Salivary Gland Neoplasms *Amer. Jour. Surg. Path* 1993 17:410-414

Yu et al. Ultrasensitive Time-Resolved Immunofluorometric Assay of Prostate-Specific Antigen in Serum and Preliminary Clinical Studies *Clin. Chem.* 1993 39:2108-2114

Yu et al. Immunoreactive Prostate-Specific Antigen Levels in Female and Male Breast Tumors and its Association with Steroid Hormone Receptors and Patient Age *Clin. Biochem.* 1994 27:75-79 --

Signed and Sealed this

Eighth Day of September, 1998

Attest:

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GAGGTCCACA CACTGAAGTT                    20

( 2 ) INFORMATION FOR SEQ ID NO:2:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:2:

GCCTCCTGAA GAATCGATTC CT                                                22

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:3:

GTTGTCTTCC TCACCCTGT                                                    19

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:4:

TAAGAAACAC TCTGGTCT                                                     18

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:5:

AGCCCCAAGC TTACCACCT                                                    19

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO ( i v ) ANTI-SENSE: NO ( x i ) SEQUENCE DESCRIPTION: SEQ ID NO:6:

CACAATCCGA GACAGGAT          18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

GCCCACTTGT CTGTAATG          18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

CAGGGCACAT GGTTCACT          18

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

TGGAGTCATC ACCTGGCCTG AGGAA          25

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

CCCAACCCTG GCAGGTGTTG TAGC                                                                          24

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

TCATCACCAT TGGCAATGAG                                                                               20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

CACTGTGTTG GCGTACAGGT                                                                               20

( 2 ) INFORMATION FOR SEQ ID NO:13:

( i ) SEQUENCE CHARACTERISTICS:
    ( A ) LENGTH: 992 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

AGCCCCAAGC TTACCACCTG CACCCGGAGA GCTGTGTNNC ACCATGTGGG TCCCGGTTGT        60

CTTCCTCACC CTGTCCGTGA CGTGGATTGG TGCTGCACCC CTCATCCTGT CTCGGATTGT       120

GGGAGGCTGG GAGTGCGAGA AGCATTCCCA ACCCTGGCAG GTGCTTGTAG CCTCTCGTGG       180

CAGGGCAGTC TGCGGCGGTG TTCTGGTGCA CCCCCAGTGG GTCCTCACAG CTGCCCACTG       240

CATCAGGAAC AAAAGCGTGA TCTTGCTGGG TCGGCACAGC CTGTTTCATC CTGAAGACAC       300

AGGCCAGGTA TTTCAGGTCA GCCACAGCTT CCCACACCCG CTCTACGATA TGAGCCTCCT       360

GAAGAATCGA TTCCTCAGGC CAGGTGATGA CTCCAGCCAC GACCTCATGC TGCTCCGCCT       420

GTCAGAGCCT GCCGAGCTCA CGGATGCTGT GAAGGTCATG GACCTGCCCA CCCAGGAGCC       480

AGCACTGGGG ACCACCTGCT ACGCCTCAGG CTGGGGCAGC ATTGAACCAG AGGAGTTCTT       540

GACCCCAAAG AAACTTCAGT GTGTGGACCT CCATGTTATT CCAATGACG TGTGTGCGCA        600

AGTTCACCCT CAGAAGGTGA CCAAGTTCAT GCTGTGTGCT GGACGCTGGA CAGGGGGCAA      660

AAGCACCTGC TCGGGTGATT CTGGGGGCCC ACTTGTCTGT AATGGTGTGC TTCAAGGTAT       720

| | | | | | | |
|---|---|---|---|---|---|---|
| CACGTCATGG | GGCAGTGAAC | CATGTGCCCT | GCCCGAAAGG | CCTTCCCTGT | ACACCAAGGT | 780 |
| GGTGCATTAC | CGGAAGTGGA | TCAAGGACAC | CATCGTGGCC | AACCCCTGAG | CACCCCTATC | 840 |
| AACCCCCTAT | TGTAGTAAAC | TTGGAACCTT | GGAAATGACC | AGGCCAAGAC | TCAAGCCTCC | 900 |
| CCAGTTCTAC | TGACCTTTGT | CCTTAGGTGT | GAGGTCCAGG | GTTGCTAGGA | AAAGAAATCA | 960 |
| GCAGACACAG | GTGTAGACCA | GAGTGTTTCT | TA | | 992 | |

( 2 ) INFORMATION FOR SEQ ID NO:14:

( i ) SEQUENCE CHARACTERISTICS:
        ( A ) LENGTH: 1462 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

| | | | | | | |
|---|---|---|---|---|---|---|
| ATTCCGCCGG | AGAGCTGTGT | CACGATGTGG | GTCCGGTTG | TCTTCCTCAC | CCTGTCCGTG | 60 |
| ACGTGGATTG | GTGCTGCACC | CCTCATCCTG | TCTCGGATTG | TGGGAGGCTG | GGAGTGCGAG | 120 |
| AAGCATTCCC | AACCCTGGCA | GGTGCTTGTG | GCCTCTCGTG | GCAGGGCAGT | CTGCGGCGGT | 180 |
| GTTCTGGTGC | ACCCCAGTG | GGTCCTCACA | GCTGCCCACT | GCATCAGGAA | CAAAAGCGTG | 240 |
| ATCTTGCTGG | GTCGGCACAG | CCTGTTTCAT | CCTGAAGACA | CAGGCCAGGT | ATTTCAGGTC | 300 |
| AGCCACAGCT | TCCCACACCC | GCTCTACGAT | ATGAGCCTCC | TGAAGAATCG | ATTCCTCAGG | 360 |
| CCAGGTGATG | ACTCCAGCCA | CGACCTCATG | CTGCTCCGCC | TGTCAGAGCC | TGCCGAGCTC | 420 |
| ACGGATGCTG | TGAAGGTCAT | GGACCTGCCC | ACCAGGAGC | CAGCACTGGG | GACCACCTGC | 480 |
| TACGCCTCAG | GCTGGGGCAG | CATTGAACCA | GAGGAGTTCT | TGACCCCAAA | GAAACTTCAG | 540 |
| TGTGTGGACC | TCCATGTTAT | TTCCAATGAC | GTGTGTGCGC | AAGTTCACCC | TCAGAAGGTG | 600 |
| ACCAAGTTCA | TGCTGTGTGC | TGGACGCTGG | ACAGGGGGCA | AAAGCACCTG | CTCGGGTGAT | 660 |
| TCTGGGGGCC | CACTTGTCTG | TAATGGTGTG | CTTCAAGGTA | TCACGTCATG | GGGCAGTGAA | 720 |
| CCATGTGCCC | TGCCCGAAAG | GCCTTCCCTG | TACACCAAGG | TGGTGCATTA | CCGGAAGTGG | 780 |
| ATCAAGGACA | CCATCGTGGC | CAACCCCTGA | GCACCCCTAT | CAACTCCCTA | TTGTAGTAAA | 840 |
| CTTGGAACCT | TGGAAATGAC | CAGGCCAAGA | CTCAAGCCTC | CCCAGTTCTA | CTGACCTTTG | 900 |
| TCCTTAGGTG | TGAGGTCCAG | GGTTGCTAGG | AAAAGAAATC | AGCAGACACA | GGTGTAGACC | 960 |
| AGAGTGTTTC | TTAAATGGTG | TAATTTTGTC | CTCTCTGTGT | CCTGGGGAAT | ACTGGCCATG | 1020 |
| CCTGGAGACA | TATCACTCAA | TTTCTCTGAG | GACACAGATA | GGATGGGGTG | TCTGTGTTAT | 1080 |
| TTGTGGGGTA | CAGAGATGAA | AGAGGGGTGG | GTACCACACT | GAGAGAGTGG | AGAGTGACAT | 1140 |
| GTGCTGGACA | CTGTCCATGA | AGCACTGAGC | AGAAGCTGGA | GGCACAACGC | ACCAGACACT | 1200 |
| CACAGCAAGG | ATGGAGCTGA | AAACATAACC | CACTCTGTCC | TGGAGGCACT | GGGAAGCCTA | 1260 |
| GAGAAGGCTG | TGAGCCAAGG | AGGGAGGGTC | TTCCTTTGGC | ATGGGATGGG | GATGAAGTAA | 1320 |
| GGAGAGGGAC | TGGACCCCCT | GGAAGCTGAT | TCACTATGGG | GGGAGGTGTA | TTGAAGTCCT | 1380 |
| CCAGACAACC | CTCAGATTTG | ATGATTTCCT | AGTAGAACTC | ACAGAAATAA | AGAGCTGTTA | 1440 |
| TACGTGAAAA | AAAACGGAAT | CC | | | | 1462 |